(12) United States Patent
Baer et al.

(10) Patent No.: US 6,887,703 B2
(45) Date of Patent: May 3, 2005

(54) TRANSFER FILM FOR LASER MICROCAPTURE

(75) Inventors: Thomas M. Baer, Mountain View, CA (US); Robert H. Reamey, Palo Alto, CA (US); David F. Head, Saratoga, CA (US); Barbara J. Wessen-Baer, Mountain View, CA (US); Ali Firouzi, Redwood City, CA (US); David Ching, Mountain View, CA (US)

(73) Assignee: Arturus Bioscience, Inc., Mountain View, CA (US)

( * ) Notice: Subject to any disclaimer, the term of this patent is extended or adjusted under 35 U.S.C. 154(b) by 565 days.

(21) Appl. No.: 09/788,117

(22) Filed: Feb. 16, 2001

(65) Prior Publication Data

US 2001/0028934 A1 Oct. 11, 2001

Related U.S. Application Data

(60) Provisional application No. 60/182,832, filed on Feb. 16, 2000.

(51) Int. Cl.$^7$ .................................................. C12N 5/00
(52) U.S. Cl. ..................... 435/325; 356/36; 427/2.11; 428/40.1
(58) Field of Search ................................ 435/325, 7.23; 428/40.1; 427/2.11; 356/36

(56) References Cited

U.S. PATENT DOCUMENTS

| | | | |
|---|---|---|---|
| 4,149,803 | A | 4/1979 | Litz |
| 4,245,003 | A | 1/1981 | Oransky et al. |
| 4,333,983 | A | 6/1982 | Allen |
| 4,559,266 | A | 12/1985 | Misasa et al. |
| 4,624,915 | A | 11/1986 | Schindler et al. |
| 4,629,687 | A | 12/1986 | Schindler et al. |
| 4,673,261 | A | 6/1987 | Hunt et al. |
| 4,731,530 | A | 3/1988 | Mikan |
| 4,857,399 | A | * 8/1989 | Vicik |
| 4,901,738 | A | 2/1990 | Brink et al. |
| 4,920,053 | A | 4/1990 | Inoue et al. |
| 4,923,294 | A | 5/1990 | Courtenay |
| 4,987,006 | A | 1/1991 | Williams et al. |
| 5,057,689 | A | 10/1991 | Nomura et al. |
| 5,077,620 | A | 12/1991 | Mauro |
| 5,096,775 | A | 3/1992 | Sato et al. |
| 5,126,877 | A | 6/1992 | Biber |
| 5,139,831 | A | * 8/1992 | Mueller |
| 5,202,230 | A | 4/1993 | Kamentsky |
| 5,280,384 | A | 1/1994 | Shibasaki |
| 5,288,996 | A | 2/1994 | Betzig et al. |
| 5,296,291 | A | 3/1994 | Mueller |
| 5,346,765 | A | 9/1994 | Maeda et al. |
| 5,391,329 | A | 2/1995 | Dougherty et al. |
| 5,468,967 | A | 11/1995 | Chan et al. |
| 5,479,252 | A | 12/1995 | Worster et al. |
| 5,492,861 | A | 2/1996 | Opower |
| 5,529,841 | A | 6/1996 | Neihof |
| 5,541,064 | A | 7/1996 | Bacus et al. |
| 5,574,077 | A | 11/1996 | Dougherty et al. |
| 5,576,264 | A | 11/1996 | Ueno et al. |
| 5,580,612 | A | 12/1996 | Hickel et al. |
| 5,585,246 | A | 12/1996 | Dubrow et al. |
| 5,665,582 | A | 9/1997 | Kausch et al. |
| 5,677,197 | A | 10/1997 | Gordon et al. |
| 5,723,290 | A | 3/1998 | Eberwine et al. |
| 5,759,781 | A | 6/1998 | Ward et al. |
| 5,763,191 | A | 6/1998 | Knoll et al. |
| 5,817,462 | A | 10/1998 | Garini et al. |
| 5,843,644 | A | 12/1998 | Liotta et al. |
| 5,843,657 | A | 12/1998 | Liotta et al. |
| 5,859,699 | A | 1/1999 | Baer et al. |
| 5,869,345 | A | 2/1999 | Chandler |
| 5,985,085 | A | 11/1999 | Baer et al. |
| 5,998,129 | A | 12/1999 | Schütze et al. |
| 6,010,888 | A | 1/2000 | Liotta et al. |
| 6,100,051 | A | 8/2000 | Goldstein et al. |
| 6,157,446 | A | 12/2000 | Baer et al. |
| 6,184,973 | B1 | 2/2001 | Baer et al. |
| 6,204,030 | B1 | 3/2001 | Liotta et al. |
| 6,215,550 | B1 | 4/2001 | Baer et al. |
| 6,251,467 | B1 | 6/2001 | Liotta et al. |
| 6,251,516 | B1 | 6/2001 | Bonner et al. |
| 6,495,195 | B2 * | 12/2002 | Baer et al. |
| 2001/0031481 | A1 | 10/2001 | Liotta et al. |

FOREIGN PATENT DOCUMENTS

| | | |
|---|---|---|
| DE | 196 03 996 A1 | 8/1997 |
| JP | 09 095657 | 4/1997 |
| WO | WO 91/07683 A1 | 5/1991 |
| WO | WO 95/23960 A1 | 9/1995 |
| WO | WO 97/13838 A1 | 4/1997 |
| WO | WO 98/35215 A1 | 8/1998 |
| WO | WO 98/35216 A1 | 8/1998 |
| WO | WO 98/36261 A1 | 8/1998 |
| WO | WO 99/17094 A2 | 4/1999 |
| WO | WO 00/06992 A1 | 2/2000 |
| WO | WO 00/34757 A1 | 6/2000 |
| WO | WO 00/68662 A1 | 11/2000 |

OTHER PUBLICATIONS

English Abstract for German Patent DE 196 03 996 A1 retrieved in Dialog database in file 12 on Dec. 12, 2001.
U.S. Appl. No. 08/800,882, filed Feb. 14, 1997, Baer et al.
U.S. Appl. No. 08/984,979, filed Dec. 4, 1997, Baer et al.
U.S. Appl. No. 09/018,452, filed Feb. 4, 1998, Baer et al.
U.S. Appl. No. 09/058,711, filed Apr. 10, 1998, Baer et al.
U.S. Appl. No. 09/121,635, filed Jul. 23, 1998, Baer et al.
U.S. Appl. No. 09/121,677, filed Jul. 23, 1998, Baer et al.
U.S. Appl. No. 09/121,691, filed Jul. 23, 1998, Baer et al.
U.S. Appl. No. 09/208,604, filed Dec. 8, 1998, Baer et al.
U.S. Appl. No. 09/357,423, filed Jul. 20, 1999, Baer.

(Continued)

*Primary Examiner*—Leon B. Lankford, Jr.
(74) *Attorney, Agent, or Firm*—Lukas IP Group; Rimas T. Lukas

(57) ABSTRACT

The present invention generally provides an improved transfer film having multiple layers for laser micro-capture of a sample. The transfer film for laser micro-capture includes distinct layers for expansion and adhesion in order to optimize the performance of the transfer film. A transfer film including a spring-back layer is also disclosed.

17 Claims, 9 Drawing Sheets

OTHER PUBLICATIONS

U.S. Appl. No. 09/562,495, filed May 1, 2000, Lossing et al.

U.S. Appl. No. 09/617,742, filed Jul. 17, 2000, Baer et al.

Banks, Rosamunde E. et al. (1999). "The potential use of laser capture microdissection to selectively obtain distinct populations of cells for proteomic analysis—Preliminary findings" *Electrophoresis* 20:689–700.

Bonner, Robert F. et al. (1997). "Laser capture microdissection: Molecular analysis of tissue" *Science* 278:1–13.

Brignole, Ed (Nov./Dec. 2000). "Laser–capture microdissection" *Modern Drug Discovery* pp. 1–3.

Chu, Samuel S. et al. (Apr. 2000). "Laser capture microdissection: Applications in Cancer Research" *Cancer Research* pp. 1–4.

Curran, S. et al. (2000). "Laser capture microscopy" *Molecular Pathology* 53(2):64–68.

DiFrancesco, Lisa M. et al. (2000). "Laser capture microdissection–guided fluorescence in situ hybridization and flow cytometric cell cycle analysis of purified nuclei from paraffin sections" *Methods in Pathology* 13(6):705–711.

Emmert–Buck, Michael R. et al. (Nov. 8, 1996). "Laser capture microdissection" *Science* 274:998–1001.

Emmert–Buck, Michael R. et al. (Apr. 2000). "Molecular profiling of clinical tissue specimens. Feasibility and applications" *American Journal of Pathology* 156(4):1109–1115.

Fend, Falko et al. (1999). "Immuno–LCM: Laser capture microdissection of immunostained frozen sections for mRNA analysis" *American Journal of Pathology* 154(1):1–6.

Fend, Falko and Raffeld, Mark (Sep. 2000). "Laser capture microdissection in pathology" *American Journal of Pathology* 53(9):666–672.

Friend, Tim (Aug. 5, 1997). "Microdissection breakthrough lets scientists isolate those involved in tumor growth" *USA Today* Section 4D pp. 1–3.

Geduspan, Jane S. and Solursh, Michael (1992). "A growth–promoting influence from the mesonephros during limb outgrowth" *Devel. Biology* 151(1):242–250.

Goldstein, Seth R. et al. (Nov. 1, 1998). "Thermal modeling of laser capture microdissection" *Applied Optics* 37(31):7378–7391.

Goldsworthy, Susan M. et al. (1999). "Effects of fixation on RNA extraction and amplification from laser capture microdissected tissue" *Molecular Carcinogenesis* 25:86–91.

Haber, Seth L. (Sep. 1999). "Future Innovations in Pathology: PixCellated" *CAP Today* pp. 1–2.

Isenberg, G. et al. (May 1976). "Cell surgery by laser micro–dissection: a preparative method" *J. Microscopy* 107, Pt 1:19–24.

Jones, Chris et al. (Jun. 2000). "Comparative genomic hybridization analysis of myoepithelial carcinoma of the breast" *Laboratory Investigation* 80(6):831–836.

Kubo, Yoshiaki et al. (Mar. 1, 1995). "Early detection of Knudson's two hits in preneoplastic renal cells of the Eker rat model by the laser microdissection procedure" *Cancer Research* 55:989–990.

Kuecker, Sara J. et al. (1999). "Analysis of PRL, PRL–R, TGFβ1 and TGFβ–RII gene expression in normal and neoplastic breast tissues after laser capture microdissection" *Applied Immunohistochemistry & Molecular Morphology* 7(3):193–200.

Leethanakul, Chidchanok et al. (2000). "Distinct pattern of expression of differentiation and growth–related genes in squamous cell carcinomas of the head and neck revealed by the use of laser capture microdissection and cDNA arrays" *Oncogene* 19:3220–3224.

Liotta, Lance A. and Petricoin, Emanuel F. (2000). "Beyond the genome to tissue proteomics" *Breast Cancer Research* 2(1):13–14.

Maitra, Anirban et al. (Rev. Jan. 26, 1999). "Enrichment of epithelial cells for molecular studies" *Hamon Center for Therapeutic Oncology Research and Departments of Pathology, Internal Medicine and Pharmacology, University of Texas Southwestern Medical Center* Dallas, Texas pp. 1–23.

Meier–Ruge, W. et al. (1976). "The laser in the Lowry technique for microdissection of freeze–dried tissue slices" *Histochemical J.* 8:387–401.

Murakami, Hiroshi et al. (2000). "IF–LCM: Laser capture microdissection of immunofluorescently defined cells for mRNA analysis" *Kidney International* 58:1346–1353.

Reiss, Susan M. (May/Jun. 1999). "Laser capture microdissection provides key to gene behavior" *Biophotonics International* pp. 1–2.

Relman, David A. (May 21, 1999). "The search for unrecognized pathogens" *Science* 284:1–3.

Schindler, Melvin (1998). "Select, microdissect, and eject" *Nature Biotechnology* 16:719–720.

Schütze, Karin & Lahr, Georgia (1998). "Identification of expressed genes by laser–mediated manipulation of single cells" *Nature Biotechnology* 16:737–742.

Shen, Chen–Yang et al. (Jul. 15, 2000). "Genome–wide search for loss of heterozygosity using laser capture microdissected tissue of breast carcinoma: An implication for mutator phenotype and breast cancer pathogenesis" *Cancer Research* 611:3884–3892.

Sinclair, Bob (Nov. 8, 1999). "The cell is my test tube. Micromanipulation tools for cell science" *The Scientist* 13(22):17, pp. 1–8.

Tam, Andrew S. et al. (Aug. 1, 1991). "High frequency and heterogeneous distribution of p53 mutations in aflatoxin $B_1$–induced mouse lung tumors" *Cancer Research* 59:3634–3640.

Veigel, Claudia et al. (1994). "New cell biological applications of the laser microbeam technique: the microdissection and skinning of muscle fibers and the perforation and fusion of sarcolemma vesicles" *Eur. J. Cell Biology* 63:140–148.

* cited by examiner

TRANSFER FILM FOR LASER MICROCAPTURE

CROSS-REFERENCE TO RELATED APPLICATIONS

This application claims priority to U.S. Provisional application Ser. No 60/182,832, filed on Feb. 16, 2000.

TECHNICAL FIELD

The present invention relates generally to the field of laser micro-capture, and more particularly, to a transfer film for laser micro-capture of a sample.

BACKGROUND ART

Diseases such as cancer have long been identified by examining tissue biopsies to identify unusual cells. The problem has been that there has been no satisfactory prior-art method to extract the cells of interest from the surrounding tissue. Currently, investigators must attempt to manually extract, or microdissect, cells of interest either by attempting to mechanically isolate them with a manual tool or through a convoluted process of isolating and culturing the cells. Most investigators consider both approaches to be tedious, time-consuming, and inefficient.

A new technique has been developed which can extract single cells or a small cluster of cells from a tissue sample in a matter of seconds. The technique is called laser capture microdissection (LCM). In laser capture microdissection, the operator looks through a microscope at a biological specimen such as a tissue biopsy section mounted on a standard glass histopathology slide, which typically contains a variety of cell types. A capture film is placed over the tissue biopsy section. Upon identifying a group of cells of interest within the tissue section, the operator generates a pulse from a laser. The laser pulse causes localized heating of the thermoplastic film as it passes through it, imparting to it an adhesive property. The cells then stick to the localized adhesive area of the thermoplastic film directly above them. Upon removal of the film from the biopsy tissue, the selected cells or sections of tissue are transferred along with the film. The film can be extracted in order to remove biomolecules for subsequent analysis. Because of the small diameter of the laser beam, extremely small cell clusters or single cells may be microdissected from a tissue section.

By taking only these target cells directly from the tissue sample, scientists can immediately analyze the DNA, RNA, proteins, or other biomolecules in order to characterize the activity of the target cells using other research tools. Such procedures as polymerase chain reaction amplification of DNA and RNA, and enzyme recovery from the tissue sample have been demonstrated.

Laser capture microdissection has successfully extracted cells in many types of tissues. These include kidney glomeruli, in situ breast carcinoma, atypical ductal hyperplasia of the breast, prostatic interepithielial neoplasia, and lymphoid follicles. The direct access to cells provided by laser micro-capture will likely lead to a revolution in the understanding of the molecular basis of cancer and other diseases, helping to lay the groundwork for earlier and more precise disease detection.

Another likely role for the technique is in recording the patterns of gene expression in various cell types, an emerging issue in medical research. For instance, the National Cancer Institute's Cancer Genome Anatomy Project (CGAP) is attempting to define the patterns of gene expression in normal, precancerous, and malignant cells. In projects such as CGAP, laser capture microdissection is a valuable tool for procuring pure cell samples from tissue samples.

The LCM technique is generally described in the published article: Laser Capture Microdissection, Science, Volume 274, Number 5289, Issue 8, pp 998–1001, published in 1996, the entire contents of which are incorporated herein by reference. The purpose of the LCM technique is to provide a simple method for the procurement of selected human cells from a heterogeneous population contained on a typical histopathology biopsy slide.

A typical biological specimen is a tissue biopsy sample consisting of a 5 to 10 micron slice of tissue that is placed on a glass microscope slide using fixation and staining techniques well known in the field of pathology. This tissue slice is a cross section of the body organ that is being studied. The tissue consists of a variety of different types of cells. Often a pathologist desires to remove only a small portion of the tissue for further analysis. Another typical biological specimen is a layer of cells coated from a liquid suspension.

Laser micro-capture employs a transfer film that is placed on top of the tissue sample. The film may contain dyes or pigments chosen to selectively absorb at the frequency of the laser. When the film is exposed to the focused laser beam the exposed region is heated and expands, contacting and adhering to the tissue in that region. The film is then lifted from the tissue and the selected portion of the tissue is removed with the film.

Transfer films such as a 100-micron thick ethylene vinyl acetate (EVA) film available from Electroseal Corporation of Pompton Lakes, N.J. (type E540) have been used. The film is chosen to have a low melting point of about 60° C.–90° C.

While the films employed in laser micro-capture applications have proved satisfactory for the task, a single-layered transfer film has been generally imbued with all of the necessary performance characteristics. For example, the transfer film must be capable of absorbing the optimum amount of energy from the laser for the desired activation of the film. In dye-impregnated films, the optical absorption is a function of its thickness, the type of dye and concentration of dye employed. This property of the film may be in conflict with a desire to select film thickness for other reasons. The film must also expand a desired amount and be capable of adhering to the specimen in desired locations yet substantially avoid adhesion to undesired particles. Furthermore, it is important to keep the temperature of that portion of the transfer film contacting the specimen sufficiently low to avoid damage to or change in the nature of the specimen. Also, the transfer film must be capable of being adhered to a carrier and preferably be transparent to enable observation during all stages of the collection procedures. These performance characteristics, among others, are demanded of the transfer film. The present invention is directed to providing an improved transfer film that de-couples some of the performance characteristics within the transfer film in order to optimize the performance of each.

DISCLOSURE OF THE INVENTION

In accordance with one aspect of the present invention, there is provided a transfer film for laser micro-capture of a sample including at least one expansion layer and an adhesive layer coupled to at least one expansion layer. The adhesive layer is located between the expansion layer and a sample for micro-capture. The expansion layer absorbs energy incident upon the transfer film and expands to exert a force upon the adhesive layer such that a selected portion of the sample adheres to the adhesive layer for micro-capture.

In accordance with another aspect of the present invention, there is provided a transfer film for laser micro-capture of a sample including at least one expansion layer and an adhesive layer coupled to the expansion layer. The adhesive layer is located between the expansion layer and a sample for micro-capture. The expansion layer absorbs energy incident upon the transfer film and expands to exert a force upon the adhesive layer such that the adhesive layer is deflected towards the sample and adheres to a selected portion of the sample. After adhesion, the adhesive layer retracts away from the sample.

In accordance with yet another aspect of the present invention, there is provided a transfer film for laser micro-capture of a sample including at least one expansion layer, at least one retraction layer and an adhesive layer. The retraction layer is coupled to the expansion layer, and the adhesive layer is coupled to the retraction layer. The adhesive layer is located between the retraction layer and a sample for micro-capture. The retraction layer is located between the expansion layer and the adhesive layer. The expansion layer absorbs energy incident upon the transfer film and expands to exert a force upon the retraction layer and adhesive layer such that the retraction layer and the adhesive layer are deflected towards the sample and a selected portion of the sample adheres to the adhesive layer for micro-capture. After adhesion, the retraction layer with the attached adhesive layer retracts away from the sample.

In accordance with yet another aspect of the present invention, there is provided a transfer film for laser micro-capture having a first layer and a second layer. The first layer is thermally coupled to at least a first energy-absorbing substance selected to absorb energy within a first spectrum. The second layer is thermally coupled to at least a second energy-absorbing substance selected to absorb energy within a second spectrum. The first layer provides a first expansion upon activation by at least a first laser pulse of energy within the first spectrum to exert a force on the second layer such that a portion of the second layer is moved towards the sample at least a first distance. The second layer provides a second expansion upon activation by at least a second laser pulse of energy within the second spectrum such that the portion of the second layer moves towards the sample a second distance.

BRIEF DESCRIPTION OF THE DRAWINGS

The foregoing and other advantages of the invention will become apparent upon reading the following detailed description and upon reference to the drawings in which.

Figure 1:
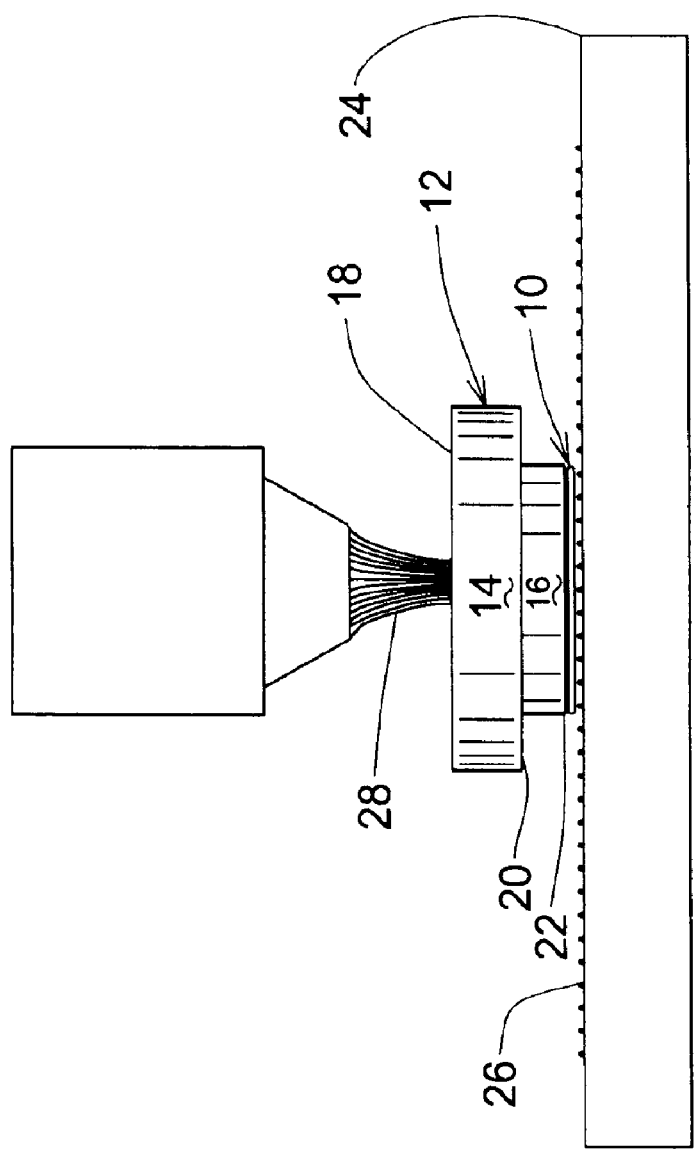
FIG. 1 is a side-elevational view of an apparatus for laser micro-capture.

While the invention is susceptible to various modifications and alternative forms, specific embodiments have been shown by way of example in the drawings and described in detail herein. However, it should be understood that the invention is not intended to be limited to the particular forms disclosed. Rather the invention is to cover all modifications, equivalents, and alternatives falling within the spirit and scope of the invention as defined by the appended claims.

BEST MODE FOR CARRYING OUT THE INVENTION

The present invention and the various features and advantageous details thereof are explained more fully with reference to the nonlimiting embodiments that are illustrated in the accompanying drawings and detailed in the following description. Descriptions of well-known components and processing techniques are omitted so as not to unnecessarily obscure the present invention.

Turning now to the drawings and referring initially to FIG. 1, there is depicted a transfer film 10 coupled to a substrate or carrier 12 in the shape of a cap. The carrier or cap 12 is adapted for a biological analysis vessel of the type disclosed in U.S. Pat. No. 5,859,699 issued on Jan. 12, 1999 entitled "Laser Capture Microdissection Analysis Vessel", U.S. Pat. No. 6,157,446 issued on Dec. 5, 2000, entitled "Laser Capture Microdissection Analysis Vessel", U.S. Pat. No. 5,985,085 issued on Nov. 16, 1999 entitled "Method of Manufacturing Consumable for Laser Capture Microdissection", U.S. Ser. No. 08/984,979 filed on Dec. 4, 1997, and U.S. Ser. No. 09/357,423 filed on Jul. 20, 1999 all of which are incorporated herein by reference in their entirety.

The cap 12 is made from an inert and, preferably, transparent plastic such as acrylic (polymethyl methacrylate). The carrier 12 is shaped as a cap and adapted to be removably coupled to an analysis vessel such as a centrifuge tube, microtiter plate, or other well-known vessels. The cap 12 has an upper portion 14 and a lower portion 16. The upper portion 14 includes a top surface 18 and a shoulder 20. The cap 12 may be provided with an identifying serial number such as a bar code label or laser-etched label that provides for easy identification and tracking of cell samples. The lower portion 16 includes a substrate surface 22 to which the transfer film 10 is coupled. The cap 12 and its configuration are not limited to this geometry.

The cap 12 of FIG. 1 is easily handled, either manually or by automated means such as an LCM apparatus of the kind disclosed in the following co-pending applications: U.S. Ser. No. 09/018,452 filed Feb. 4, 1998, U.S. Ser. No. 09/121,691 filed on Jul. 23, 1998, U.S. Ser. No. 09/121,635 filed on Jul. 23, 1998, U.S. Ser. No. 09/058,711 filed on Apr. 10, 1998, U.S. Ser. No. 09/121,677 filed on Jul. 23, 1998, U.S. Ser. No. 09/208,604 filed on Dec. 8, 1998, and U.S. Ser. No. 09/617,742 filed on Jul. 17, 2000. The cap 12 facilitates obtaining the sample and decreases the possibility of DNA contamination of the sample during handling and transport.

The cap 12 is shown positioned over a glass slide 24 and a tissue sample 26. The glass slide 24 and cap 12 are placed under a microscope objective and a laser pulse, shown diagrammatically at reference numeral 28, is directed at a selected region of the tissue sample 26 to perform the laser capture microdissection. Those of ordinary skill in the art will appreciate that an alternate configuration that may be employed is an inverted microscope wherein the tissue sample 26 may be viewed from underneath the sample slide 24. Such skilled persons will appreciate that the present invention may easily be used in such a configuration.

Suitable lasers for use in the present invention include carbon dioxide lasers (9.6–11 micrometer wavelengths), laser diodes, tunable single frequency titanium-sapphire lasers, and diode-pumped neodymium-doped, yttrium-aluminum garnet (Nd:YAG) lasers. The wavelength outputs from these lasers can preferably range from ultraviolet to infrared. A particularly desirable laser for use with the present invention is a laser diode with wavelengths between approximately 690 nm and 1300 nm. In this wavelength range, conventional glass microscope optics are highly transmissive and can be used to focus the laser.

The laser capture operation can be simply described. First, the microscope stage is centered and the transfer film 10 coupled to the cap 12 is placed in position above the tissue sample 26 on slide 24. The transfer film 10 contacts the tissue sample 26. Next, the tissue sample 26 is inspected until desired cells are located. Then, the laser activates the transfer film 10, which absorbs energy from the laser. As a result, a selected portion of the transfer film 10 expands to contact the tissue and cause adhesion of the target cells to the transfer film 10. Alternatively, the transfer film 10 is spaced from the sample 26 (noncontact laser micro-capture). In this case, the expansion of the transfer film 10 upon activation by the laser pulse 28 will simply inject a portion of the transfer film 10 into the tissue sample 26 for capturing target sample cells. Mechanical adhesion occurs as interlocking occurs when, due to heating, the thermoplastic material flows about and into the voids of the rough tissue sample surface and interlocks upon subsequent cooling.

In contact micro-capture, the transfer film 10 makes contact with a tissue section prior to activation by the laser pulse 28. Due to the friable nature of tissue sections, loose material (whole cell or macromolecular) is likely to adhere to the transfer film 10 even though the laser did not illuminate them resulting in non-specific transfer of material. If these portions are transferred to the reagent vessel, they will be digested by the reagents and appear as contaminants in the sample. It is important to prevent the loosely bound tissue areas from contacting the film 10. Reducing this problem by providing a non-stick barrier layer in contact micro-capture is described in copending application U.S. Ser. No. 09/562,495 filed on May 1, 2000, which is, in its entirety, incorporated herein by reference. Another way of reducing non-specific transfer, for example, is non-contact LCM. In non-contact LCM, the transfer film is offset or distanced a few microns from the tissue sample as described in co-pending application U.S. Ser. No. 08/984,979 filed on Dec. 4, 1997.

After the activated portion of the transfer film 10 solidifies, the film 10 is withdrawn. The physical interface between the transfer film 10 and the selected cell area of the sample intended for microdissection causes the transfer film 10 when it is withdrawn to "pull" the selected sample area from the remainder of the specimen. Micro-capture occurs.

For laser micro-capture, the transfer film 10 is adapted for absorbing energy delivered by the laser pulse 28 or multiple pulses of the same or different energy wavelengths. The transfer film 10 is further adapted for expanding and adhering to the target cells. Typically, a single layer within the transfer film 10 performs all of the functions of energy absorption, expansion and adhesion; and a suitable material having all of the desired characteristics is selected. According to one aspect of the present invention, the transfer film 10 includes more than one layer such that one or more of the functions of absorption, expansion and adhesion are de-coupled into one or more separate layers. By separating one or more of the functions into separate layers within the transfer film 10, the performance of transfer film 10 is increased by optimizing the materials selected to perform each function or combination of functions.

A variety of thermoplastic polymer films are widely used as heat activated adhesives that are suitable for the transfer film 10. It is preferable to use a polymer film having a high melt index range such as greater than 100 dg/min so that it is activatable at lower temperatures to avoid damage to or change in the nature of the tissue sample 26. Therefore, it is important that the temperature of the portion of the transfer film contacting the sample is below approximately 100° C., preferably below approximately 80° C., and more preferably below approximately 60° C. Melt index is measured according to ASTM D1238 in which a sample of polymeric material is melted isothermally in a heated chamber and then pushed out of a capillary orifice under a fixed load. The amount of extruded material over time is measured and the melt flow rate (index) is determined in decigrams/minute.

Figure 2:
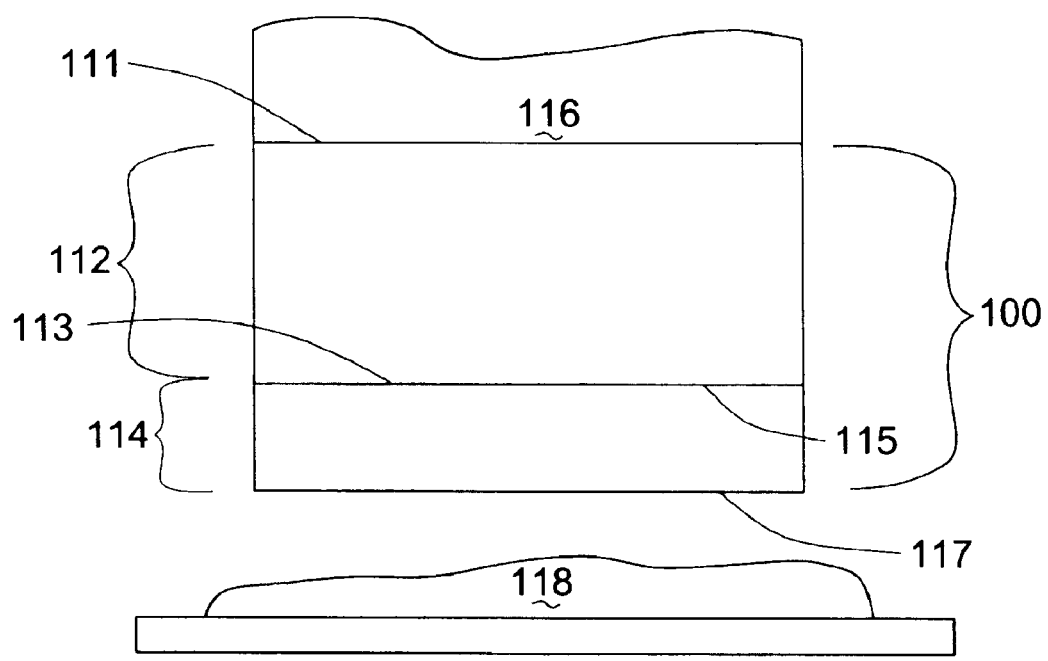
FIG. 2 is a side view of a transfer film, carrier, and sample of the present invention.

Turning now to FIG. 2, a cross sectional view of a transfer film 100 is shown. The transfer film 100 includes an expansion layer 112 having a first surface 111 and a second surface 113. The transfer film 100 is coupled to a substrate cap 116 at the first surface 111 and to an adhesive layer 114 at the second surface 113 such that the expansion layer 112 is located between the adhesive layer 114 and the substrate cap 116. The adhesive layer 114 includes a first surface 115 and a second surface 117. The thickness of the transfer film 100 is approximately greater than approximately 10 $\mu$m.

The expansion layer 112 includes a material adapted for expansion that is made from a wide variety of electromagnetically or thermally activatable materials. For conventional one layer micro-capture, the polymer must be chosen such that it has "hot-melt" characteristics, in that it becomes adhesive as its temperature is raised. In particular, ELVAX™ 410, 200 and 205 are suitable resins of EVA that are commercially available from DuPont E. I. de Nemours and Company of Wilmington, Del. Generally, the EVA should have a high-melt index indicated by a low viscosity and low molecular weight. EVA, among plastics, has a uniquely low melting range, which can be controlled by its manufacture. Such manufacture control can include the addition of a variety of ingredients (e.g. co-polymers) to adjust the melting point and other properties of the EVA. Persons of ordinary skill in the art will recognize that other materials having desirable properties may also be employed.

The said limitation of needing a polymer that simultaneously acts as an energy-adsorbing medium, expands, wets and adheres to the sample, does not hold for the expansion layer of the present invention, thus allowing any polymer that merely expands with the absorption of energy to be used. This allows the use of essentially any polymeric material which can absorb the energy or contains an energy adsorbing substance, and which can melt-flow during the application of a laser pulse. These include polymers such as one or more of the following: silicone, polyimides, polyesters, polyethers, fluoropolymers, polyethyelene and it's copolymers such as ethylene vinyl acetate (EVA), polyurethanes, polyvinyl acetates, ethylene-methyl methacrylate, polycarbonates, ethylene-vinyl alcohol copolymers, polypropylene, and expandable or general purpose polystyrenes. Additives to modify the base polymers including plasticizers, antioxidant stabilizers, pigments or dyes can be used as known to the persons skilled in the art.

The expansion layer 112 comprising EVA, for example, expands isotropically when it is exposed to the energy from the laser. As an approximation, the EVA film expands approximately 12–15% downward and upward when it is exposed to the charge from the laser. The substrate cap 116 may restrict upward expansion. The material used as the expansion layer 112 can be an EVA of the type used for conventional laser micro-capture, but the restriction on melt index and melt temperature is not as great in the present invention because the expansion layer does not have to come into direct contact with the biological sample. Hence, expansion and adhesion are de-coupled in the transfer film of the present invention such that expansion is provided by the expansion layer 112 and adhesion is provided by the adhesive layer 114. This means that, for instance, EVAs with melt index values below 200 dg/min could be suitable for the expansion layer and a lower sample contact temperature can be achieved because the expansion layer 112 does not contact the sample for adhesion.

The performance properties for the adhesive layer in this multilayered construction is wetting and adhesion to the sample. As such, several different class of materials can be utilized. In one embodiment, the adhesive layer 114 in FIG. 2 can be an ordinary pressure sensitive adhesive (PSA), a hot melt adhesive, or a UV- or electron-beam-curable adhesive or coating. For the PSA category, which can be of solvent-based, water-based, or hot-melts subcategories, the polymeric material can be a rubber (natural, butyl, or styrene-butadiene rubber), a block copolymer such as styrene-ethylene/butadiene-styrene (SEBS), styrene-isoprene-styrene (SIS), or other polymers (polybutene, polyvinylether, acrylics, ethylene-vinyl acetate, atactic polypropylene, silicone). The pressure sensitive adhesive may also contain tackifying agents to increase the adhesiveness of the capture polymer in order to more effectively microdissect the selected area of tissue without compromising the other properties needed for microdissection. Generally, the tackifying agents must be compatible with the thermoplastic material to which they are added. The tackifying agents must be at least partially soluble and not completely phase separated. As such, tackifying resins such as aliphatic, aromatic, mixed hydrocarbons, rosins, and terpenes can be used. Also, the addition of tackifying agents must maintain the optical clarity and transparency of the capture polymer and not compromise the tensile strength to the point that cohesive failure occurs in the polymer when removing the selected portion of the tissue. Furthermore, the tackifying agent must also not interfere with subsequent steps of extraction and molecular analysis of the tissue. The amount of tackifying agent is approximately 2 wt. % to 50 wt. %, preferably, 8 wt. % to 20 wt. % of the total formulation. The softening point of suitable tackifying agents is between approximately 18° C. and 99° C. The softening point of thermoplastics is defined as the temperature at which the polymers begin to show viscoelastic movement under particular combinations of load and rate of temperature rise. Two ASTM methods: D1525 "Test Methods for Vicat Softening Temperature of Plastics" and E28 "Test Method for Softening Point by Ring-and-Ball Apparatus" are commonly used. In addition to the important tackifying agents described, common additives, such as plasticizers, antioxidant stabilizers, thioxotropic agents, coupling agents, UV absorbers, and pigments or dyes can be employed. For the hot melt adhesives category, polymeric material can be EVA copolymers, acid terpolymers, EMA copolymers, ethylene n-butyl acrylate copolymers, low density polyethylene, polypropylene, polyisobutylene, polybutene, polyamides, or sulfonated branched polyester. Tackifying agents and additives are the same as described above. UV-curable adhesives can be either free-radically or cationically initiated, and most commonly are based on acrylates, methacrylates, oe epoxy-based. EB-curable adhesives are most commonly based on vinyl chemistry, optionally in combination with pro-radiation additives.

As an example of a case where the adhesive layer 114 is a pressure sensitive adhesive, this layer is preferably un-doped such that a low sample contact temperature upon adhesion can be maintained. The thickness of the adhesive layer 114 is approximately 0.1–10 $\mu$m, preferably less than approximately 5 $\mu$m.

Generally, the pressure sensitive adhesive material is coupled to an expanding, heat-activated portion of the transfer film 100 such as the expansion layer 112. The expanding portion of the expansion layer 112 pushes on the pressure sensitive adhesive material such that sufficient pressure is exerted in contact with the tissue sample 118. Application of sufficient pressure causes the pressure sensitive adhesive to flow. When the pressure is removed, the melt strength of the polymer is high enough to hold and adhere to the target cells which are subsequently excised or captured. One advantage of using a pressure sensitive adhesive within the adhesive layer 114 is that the adhesive layer 114 that comes into contact with the tissue sample 118 is not as hot as the expanding layer 112. This advantage provides for a more gentle capture and may facilitate the capture of live cells.

The expansion of the polymer occurs through several mechanisms. One mechanism is the melting of crystallites of a semicrystalline polymer, another mechanism is the solid to liquid transition, a third mechanism is the simple bulk expansion of a material with temperature represented by the thermal coefficient of expansion, and a fourth mechanism is the generation of gas within the expansion layer.

One benefit of the generation of gas bubbles is the increased expansion that they provide over the expansion due to the polymer solid-solid, solid-liquid, and bulk thermal expansions. The gas can be from expansion of the small amounts of small molecules in the film (water, residual solvents, dissolved gasses, etc.), volatilization of the polymer itself, and/or from molecules generated from thermal degradation. Blowing agents can be added to the film in order to facilitate gas generation. The term blowing agent is used to refer to a polymer additive, which generates gas bubbles in the polymer. These agents are commonly used to create foamed polymers. "Physical" foaming agents are compounds, which expand within the polymer without an associated chemical reaction. An example of a physical foaming agent is a small molecule, commonly a hydrocarbon, fluorocarbon, or chlorocarbon with a relatively low boiling point, which is dissolved into a polymer, and is then induced to foam by the introduction of thermal energy and/or a reduction of pressure. "Chemical" foaming agents generate gasses via a chemical reaction, usually resulting in the generation of gasses such as nitrogen, $CO_2$, hydrogen, etc. Examples of chemical foaming agents are azo compounds, hydrazides, peroxides, and carbonates. Some of these materials decompose exothermically, some decompose endothermically. Specific compounds which can be used are azodicarbonamide and derivatives, sulfohydrazides such as 4,4'oxybisbenzenesulfonyl hydrazide, sodium salts of carbonic acid, and 5-phenyl tetrazole. The chemical foaming agents generate gasses when exposed to energy, usually in the form of heat or light.

Blowing agents are advantageous in that the gas is generated in a controlled manner at a controlled temperature. It is desired to generate the gas in a small region in order to perform laser capture in a small spot. By generating the gas at a relatively low temperature, the bubble can be formed at relatively low laser power, and with a relatively short pulse. The short pulse allows the heat to create the bubble in a small region before thermal diffusion can expand that region undesirably far from the irradiation region.

One embodiment of the present invention is to have at least one layer of the transfer film 100, such as the expansion layer 112, contain a thermally activated foaming agent thermally coupled to an energy-absorbing substance of the type discussed below, including an infrared absorbing dye of the type discussed below. The dye, for example, absorbs energy from the laser causing heating of the expansion layer polymer, which also causes the blowing agent to generate gas in the film 100. Alternatively, the dye can be in a layer (not shown) separate from the blowing agent. In some cases, it is advantageous to locate the layer, such as the expansion layer 112, containing the blowing agent between the adhesive layer 114 and the cap 116 such that the bubble formed by the generated gas pushes the adhesive layer 114 into the tissue below. If a photochemically activated blowing agent is used, the need for a separate dye for heat absorption can be reduced or eliminated.

Still referencing FIG. 2, the transfer film 100 is also adapted for energy-absorption such that at least one layer of the transfer film 100 absorbs energy incident upon the transfer film 100 such as energy from the laser beam or other activating light source to activate the transfer film 100. A variety of wavelengths of electromagnetic energy can be used in the practice of the invention provided that suitable materials are used. In particular, it is important that the transfer layer 100 absorbs sufficient energy at the chosen wavelength or wavelengths to provide expansion of at least the expansion layer 112 in the targeted region as well as to impart any desirable adhesion characteristics to the adhesion layer 114. For a transfer film 100 comprising thermoplastic materials such as EVA, a wavelength of approximately 0.3 $\mu$m to approximately 10.0 $\mu$m is preferred as these materials intrinsically absorb in this range. It is preferred that the wavelengths for laser activation and energy absorption be chosen outside the normal range used for microscopic imaging. For example, a variety of wavelengths from the laser can be employed for reproducible microtransfer of tissue.

To enhance energy absorption, the transfer film 100 can include an energy-absorptive substance. For example, the expansion layer 112 may be thermally coupled to an energy-absorptive substance and/or the adhesive layer 114 may be thermally coupled to an energy-absorptive substance. Thermal coupling merely requires that heat in one of the layer or layers is capable of being directly or indirectly transported to another layer or layers. As is well known, thermal transport can be achieved by conduction, convection, or radiation.

There are many well-known energy-absorptive substances that are capable of being thermally coupled to the transfer film 100 either to the expansion layer 112 or adhesive layer 114 or both. For example, the energy-absorptive substance can include an absorptive dye. This dye can be either a broadband absorptive dye or a frequency-specific absorptive dye. A broadband absorptive dye is one capable of absorbing a portion of the electromagnetic spectrum, preferably a portion within a range having a wavelength of approximately 0.3 $\mu$m to approximately 10.0 $\mu$m. The broadband absorptive dye can have a relatively broad absorption line or absorb energy throughout the visible region of the spectrum so that the dye does not affect the color spectrum of the transmitted light that is used to illuminate the sample. Broadband absorptive dye can provide strong absorption of a range of wavelengths without altering the transparency of the transfer film 100 to visible light. Generally, the expansion layer 112 has a high dye level (optical density >0.4).

It is also possible to thermally couple infrared absorbing dyes to the transfer film 100 to provide strong absorption at other specific infrared wavelengths without altering the films transparency to visible light. Such dyes are preferably infrared absorbing dyes, which are readily soluble in plastic films and have a high extinction coefficient, narrow infrared or near-infrared absorption (e.g. from 750 to 1500 nm, and more particularly from 750 to 1100 nm) bands that can be matched to a variety of infrared or near-infrared lasers (including laser diodes). If the focused pulse of electromagnetic radiation (e.g., a laser pulse) is delivered at wavelengths that are strongly absorbed by the film, then the film may be efficiently activated.

The response of the system described here may involve temporal dependence as well. The thenno-mechanical features may be optimized in light of pulsing at least a first laser to achieve the appropriate change in volume of the first expansion layer 112 whereupon a second laser is pulsed to activate a spectrally separate layer such as a thermally coupled adhesive layer 114. This multiple pulse technique is utilized to provide broad area, temporary expansion of the expansion layer 112 coupled with a spatially selective (approximately 1 $\mu$m to 10 $\mu$m) expansion of the adhesive layer 114. The expansion layer 112 would then relax, effecting capture of the desired tissue. Film thickness and absorbance are tailored for optimal temporal, optical and spectral performance. The correspondingly appropriate pulses of the correct wavelength, duration and spot-size would address these properties.

For example a first layer such as the expansion layer 112 is thermally coupled to at least a first energy-absorbing substance selected to absorb energy within a first spectrum. The second layer such as the adhesive layer 114 is thermally coupled to at least a second energy-absorbing substance selected to absorb energy within a second spectrum. The first layer provides a first expansion upon activation by at least a first laser pulse of energy within the first spectrum to exert a force on the second layer such that a portion of the second layer is moved towards the sample at least a first distance. The second layer provides a second expansion upon activation by at least a second laser pulse of energy within the second spectrum such that the portion of the second layer moves towards the sample a second distance. Hence, any one or more layers such as the expansion layer 112 and/or the adhesive layer 114 may be thermally coupled or doped with at least one independently addressable, spectrally selective, energy absorbing substance.

Many types of dyes could be considered for infrared absorption, since most classes of dyes that absorb energy having wavelengths in the visible spectrum can be extended in range of wavelength absorption by molecular modification. Phthalocyanines, cyanines and Epolight 4019 from Epolin Inc., of Newark, N.J., have been among the most popular dyes because of stability, ease of preparation, solubility, optical and other properties including narrow band, high extinction coefficient and high temperature plastic processing. Moreover, the number of possible modifications of these dyes is very large because various central metal atoms which can be added and a variety of ring attachments, which can be made to them. Naphthalocyanine dyes are examples of near-infrared absorbing dyes.

Some examples of naphthalocyanine absorptive dyes include one or more of the following: tin(IV) 2,3-naphthalocyanine dichloride; silicon(IV) 2,3-naphthalocyanine dihydroxide; silicon (IV) 2,3-naphthalocyanine dioctyloxide; and vanadyl 2,11,20,29-tetra-tert-butyl-2,3-naphthalocyanine. Vanadyl 2,11,20,29-tetra-tert-butyl-2,3-naphthalocyanine, for example, absorbs near infrared with a narrow absorption peak at 808 nm which closely matches the emission wavelength of laser diodes made of gallium arsenide with aluminum doping (AlGaAs) widely used to pump solid state Nd:YAG lasers. Some of the naphthalocyanine dyes are moderately soluble in EVA polymers and other similar thermoplastic materials. They are stable compounds with heating to approximately 300° C. and do not exhibit adverse photochemistry, which might affect biological macromolecules in the tissue.

In the case where the energy-absorptive substance is an energy-absorptive dye, the transfer film 100 is doped with the dye using techniques well known in the art. For example, the dye may be mixed with the melted bulk plastic at an elevated temperature and then manufactured into a film using standard film manufacturing techniques. The doped film itself may then constitute the transfer film 100 or the doped film of thermoplastic may be thermally coupled as a separate layer such as the expansion layer 112 or adhesive layer 114 or both to form the transfer film 100.

Alternatively, organic solvents incorporating dye may be used to dope the expansion layer 112 and/or adhesive layer 114 by immersion into the solvent followed by diffusion of the dye-containing solvent. The concentration of dye in solution and the duration of immersion can be adjusted to obtain the desired concentration and depth of diffusion of the dye. Generally, the concentration of dye will result in a gradient of dye concentration such that the concentration of dye will decrease in a direction inward from the surface where the dye concentration will be greater relative to the concentration of dye inwards from the surface. The solvent can then be removed, for example, by vacuum degassing.

Alternatively, a coating material may be applied to the transfer film. For example, dye-containing solvent may be applied to the expansion layer 112 and/or adhesive layer 114 and followed by evaporation of the solvent. The concentration of dye may also form a gradient in a direction away from the surface of the coated thermoplastic as it penetrates into the film with a depth determined by the duration and amount of solvent applied to the film. Coatings on the low-temperature film surfaces can be applied by spraying, dipping, or spreading. To apply the coatings evenly it may be necessary to prepare the surface of the thermoplastic by plasma etching to make it amenable to solution wetting and provide satisfactory film adhesion.

Various naphthalocyanine compounds, for example, are soluble in solvents such as methylene chloride or chloroform. Dissolving a dye into a solvent to form a dye coating is also possible with a metal naphthalocyanine compound that is obtained by synthesizing a metal-free naphthalocyanine compound and introducing a metal therein. This process enables introduction of almost all metals and a choice may be made from a wide variety of metal naphthalocyanine compounds. The naphthalocyanine compounds have a maximum absorption wavelength in the range of 550 to 1100 nm. Thus, they find use as photo-functional materials accommodating the wavelength of certain lasers.

The transfer film 100 may include other absorptive substances including non-dye materials that are thermally coupled to the expansion layer 112 and/or adhesive layer 114. Non-dye energy absorbers include a plurality of Fullerines (i.e., Bucky Balls, e.g., C60), or a metal film of nichrome or titanium. The transfer film 100 may include the metal film via doping or as a separate layer that is thermally coupled to the expansion layer 112 and/or the adhesive layer 114. For example, metal films of nichrome or titanium can be deposited on a surface which is then attached to the thermoplastic by first evaporating a very thin layer of metal film (approximately 10–100 Å) onto a transparent support film such as mylar or polyester using a deposition technique such as sputtering. The deposition is halted when the appropriate absorption level of the film is reached. This is a procedure that is well known to those skilled in the art of thin film coating. If necessary, the thermoplastic material, such as EVA, may be dissolved in a solvent such as methylene chloride to reduce its viscosity as is well known in the art. Buckminsterfullerene, available as product #379646 from Sigma Chemical Company of St. Louis, Mo., can also be used to dope the thermoplastic by mixing the Buckminsterfullerene with heated EVA, for example, in a concentration that provides the desired energy-absorption. Broadband absorbers are discussed in co-pending application U.S. Ser. No. 08/800,882 filed on Feb. 14, 1997 which is incorporated herein by reference in its entirety. Furthermore, a polymer nanocomposite, containing thermally conductive nanoparticles (e.g., nano alumina, nano-boron nitride, etc.) can be employed in which the filler particle size is at most 25% of the visible wavelength, such that light scattering is minimized, leading to a highly transparent, yet thermally conductive polymeric film.

Figure 3:
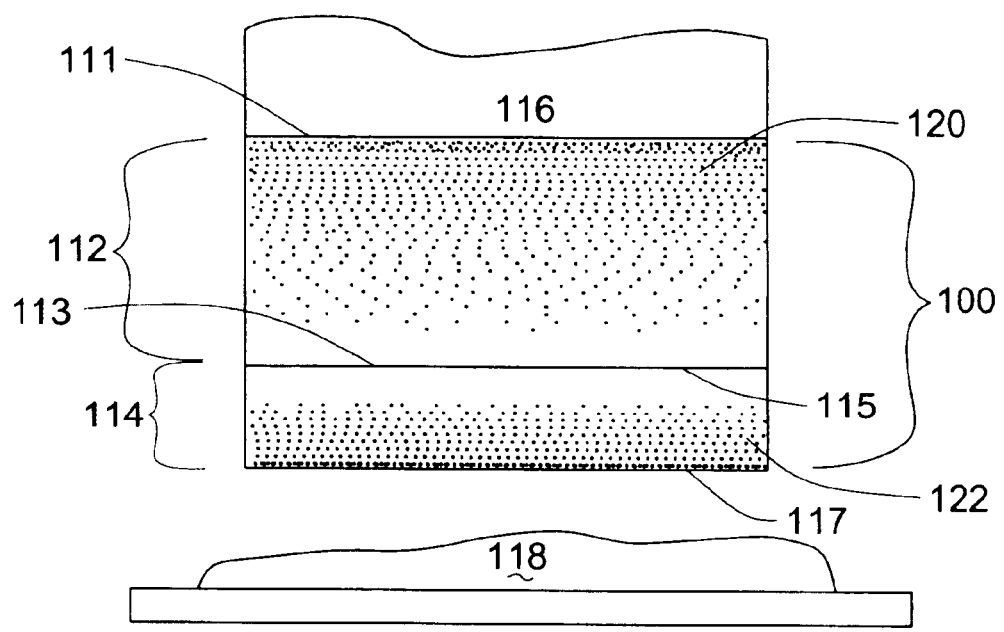
FIG. 3 is a side view of a transfer film, carrier, and sample of the present invention.

As described above, the adhesive layer 114 is activatable and adheres to the sample 118 when activated by the laser beam. The layer serving as an adhesive layer 114 may contain one or more energy-absorptive substances of the type discussed above and thermally coupled thereto in the manner discussed above with respect to the expansion layer 112. Alternative to such homogenous distribution of dye particles in the expansion and/or adhesive layers described in FIG. 2, the adhesive layer 114 may be doped with energy-absorbing dye such that a concentration gradient 122 is formed within the layer 114 as shown in FIG. 3. Here, the adhesive layer 114 is shown to be doped, for example, with a dye containing solvent such that the dye diffuses into the adhesive layer 114 at the second surface 117. The invention is not so limited and the adhesive layer 114 can be doped at the first surface 115 and/or second surface 117. Similar to such concentration gradients related to the adhesive layer, a concentration gradient can be employed in the expansion layer 112. This can be achieved by doping the expansion layer 112 with a dye-containing solvent such that the dye diffuses into the expansion layer 112 at the first surface 111. The invention is not so limited and the expansion layer 112 can be doped at the second surface 113. Moreover, the expansion layer 112 is thermally coupled to an energy-absorbing substance at its first surface 111 and/or its second surface 113. Different methods of thermally coupling the expansion layer 112 to an energy-absorbing substance include doping to form a concentration gradient, doping to form a substantially uniform concentration, coupling a separate energy-absorptive layer that may be doped or un-doped as discussed above and are within the scope of the present invention. Any combination of doping the first and/or the second surfaces 111, 113 is thus within the scope of the invention. Furthermore, the expansion layer 112 has a softening point of approximately 60° C. to approximately 150° C. and a thickness of approximately 10 µm to 80 µm. The softening point of the adhesive layer 114, which comes into contact with the sample, is generally less than the softening point of the expansion layer 112, and preferably less than 90° C.

With regards to the method of making or manufacturing the multilayered transfer films of the current invention can be divided into several categories. In the first, conventional polymer processing techniques such as co-extrusion and lamination, the latter can be operated continuously as in a calendaring process, or as a batch-process as in compression molding. For example, the transfer film 100 can be manufactured by passing two distinct layers 112 and 114 through lamination rollers. In addition to these melt processes, a thin layer (for example, that of an adhesive layer) can be solvent coated onto another layer (for example, the expansion layer). These solvent-based processes include, but are not limited to, spray coating, gravure coating, and dip coating.

Figure 4:
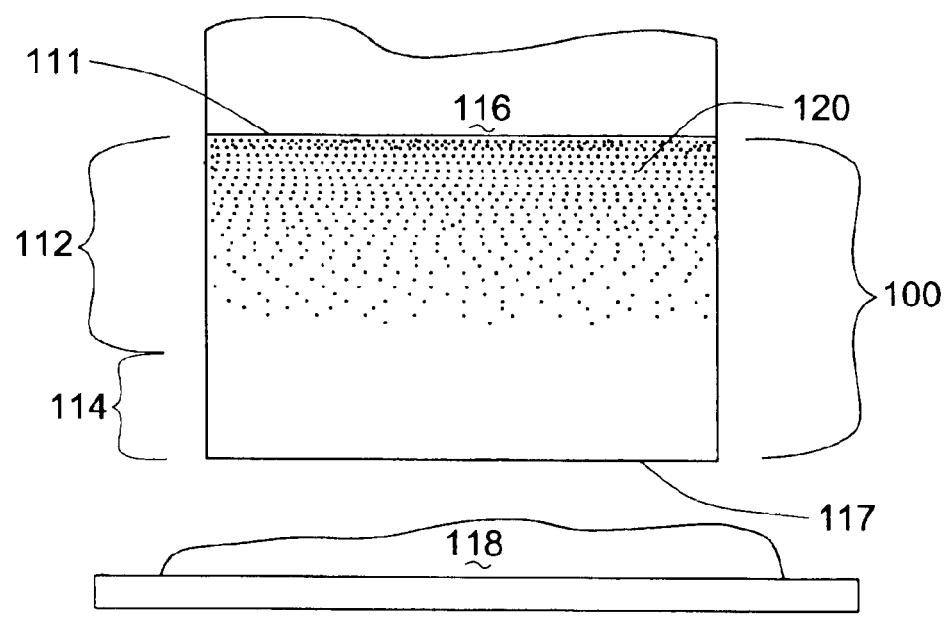
FIG. 4 is a side view of a transfer film, carrier, and sample of the present invention.

In addition to a multilayer construction, the current invention is not so limited, and it is understood that a transfer film 100 having an expansion layer 112 and an adhesive layer 114 can be formed via doping a single layer in such a manner as to effect dual layer performance using energy-absorbing substances and methods described above. This is illustrated in FIG. 4. Here, the transfer film 100 is a single layer of at least one polymer of the type discussed above in reference to the expansion layer 112 that is doped with at least one energy-absorbing substance of the type and in the manner described above such that an expansion layer 112 and an adhesive layer 114 are thereby formed. Although FIG. 4 illustrates doping from a first surface 111 such that a concentration gradient 120 is formed with a high concentration of dopant at the first surface 111 relative to a second surface 117, the invention is not so limited and a more uniform concentration of energy-absorbing substance can be formed. Basically, the concentration of energy-absorbing substance in the expansion layer 112 can be tailored in shape as well as concentration. Although the expansion layer 112 in FIG. 4 is readily discernable, the expansion layer 112 does not have a distinct second surface 113 separating the expansion layer 112 from the adhesive layer 114 nor does the adhesive layer 114 have a distinct first surface 115 as in FIG. 2 or 3. An energy-absorptive substance need not be employed. Instead, dual-layer performance can be achieved by fabricating a single layer of one or more polymers of the type described in reference to the expansion layer 112 above.

With regards to the choice of a polymeric material for this single-layer construction, once again, one is limited to a material that simultaneously acts as an energy-adsorbing medium, expands, wets and adheres to the sample, for example an EVA material with relatively high melt index. Moreover, as mentioned above, EVA or other thermoplastics can be doped by applying a solvent containing a suitable dye to one side of the transfer film 100. The dye will penetrate into the thermoplastic film with a depth determined by the duration, amount of solvent applied to the film, and the concentration of dye within the solvent. The concentration of the dye and the amount of solvent can be adjusted to provide a concentration gradient of a specific magnitude. The dye is generally dissolved into the solvent at a concentration of approximately 0.001 wt. % to 1 wt. %. The solvent is chosen such that it completely dissolves the dye in the desired concentration range, and that it swells the polymer. For the polymers described herein, with naphthalocyanine dyes, solvents such as methylene chloride chloroform, toluene, and cyclohexane are suitable. It is most convenient to operate at room temperature. With the solvent and polymers described herein, the times needed will be from seconds to hours depending on the desired amount of dye doping. In many cases, dye penetration on the order of approximately 10 µm to 20 µm is desired.

Another method of doping thermoplastic film is to place a barrier that is impenetrable to the dye-containing solvent on one side of the film, leaving the other side accessible to the solvent/dye solution. The film can then be dipped into the solvent/dye solution and left for an appropriate amount of time to develop a specific gradient within the thermoplastic. The concentration of the dye in the solvent, the type of solvent and its aggressiveness to EVA, the temperature of the solvent and the amount of time the film is in contact with the solution can all be adjusted to provide the appropriate gradient. The solvent can then be removed, for example, by vacuum degassing.

When activated by a laser beam, the expansion layer begins to soften and expand in a direction toward the sample 118. Any expansion of the expansion layer 112 in a direction toward the substrate cap 116 is contained by the rigid cap 116. Hence, a force by the expanding expansion layer 112 is exerted upon the adjacent adhesive layer 114. The amount of force exerted by the expansion layer 112 can be customized by selecting materials and thicknesses for the desired mechanical and thermal response.

The response of the system described here may involve temporal dependence as well. The thermo-mechanical features may be optimized in light of pulsing a first laser to achieve the appropriate expansion of the expansion layer 112 whereupon a second laser is pulsed to activate a spectrally separate layer such as a thermally coupled adhesive layer 114. This technique could be utilized to provide a broad area temporary expansion of the expansion layer 112 coupled with a spatially selective (i.e. 1–10 micron level) expansion of the thermally coupled adhesive layer 114. The expansion layer 112 would then relax, effecting capture of the desired tissue. Film thickness and absorbance are tailored for optimal temporal, optical and spectral performance. Hence, any one or more layers such as the expansion layer 112 and/or the adhesive layer 114 may be doped with at least one independently addressable, spectrally selective energy-absorbing substance.

Figure 5:
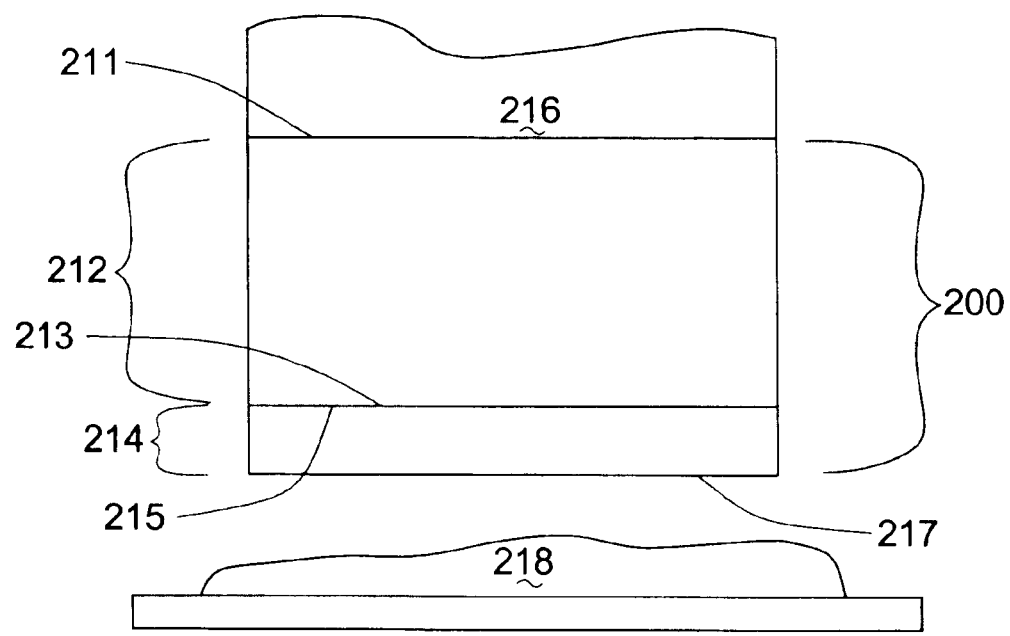
FIG. 5 is a side view of a transfer film, carrier, and sample of the present invention.
Figure 6:
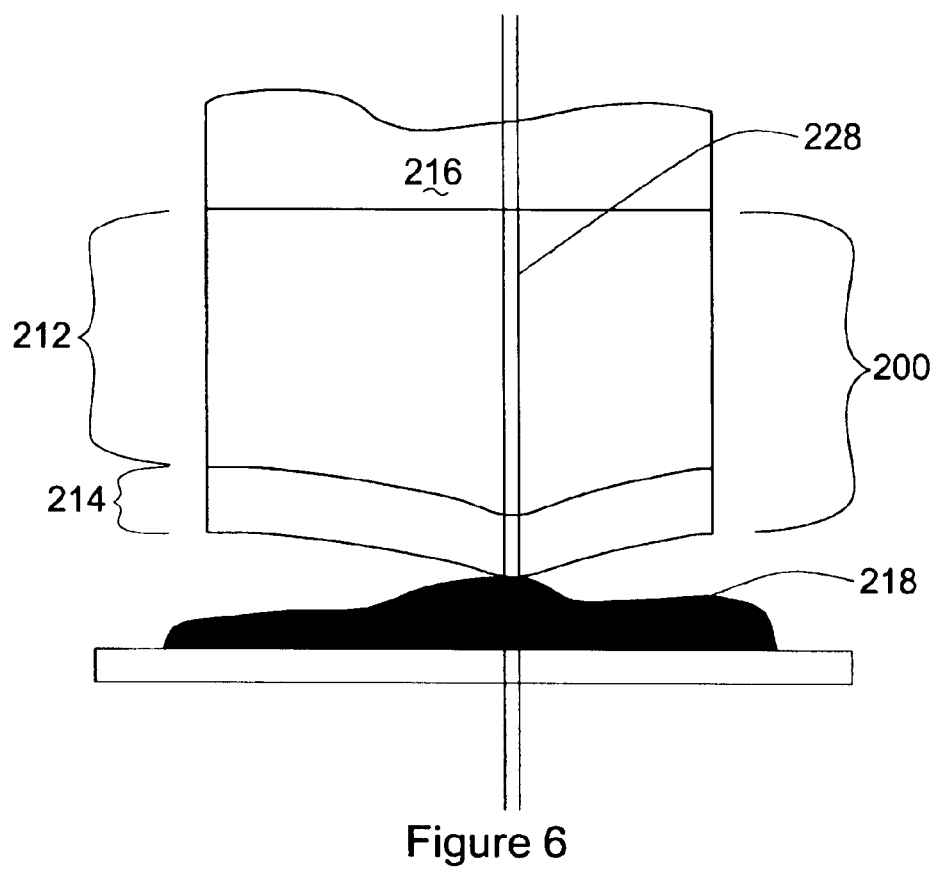
FIG. 6 is a side view of a transfer film, carrier, and sample of the present invention.
Figure 7:
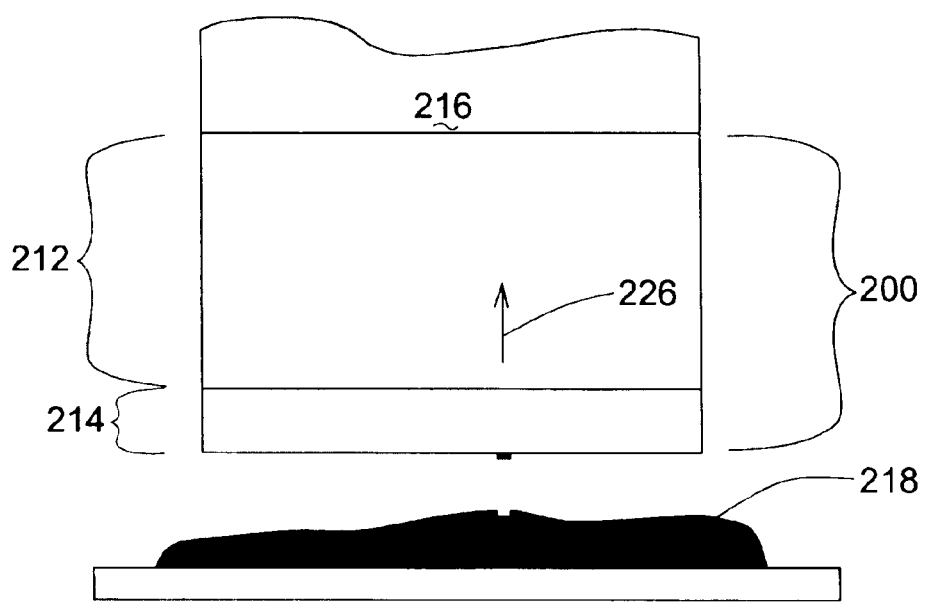
FIG. 7 is a side view of a transfer film, carrier, and sample of the present invention.

Referring now to FIGS. 5–7, a cross sectional view of a transfer film 200 attached to a cap 216 is shown. The transfer film 200 includes an expansion layer 212 and an adhesive layer 214. The expansion layer 212 includes a first surface 211 and a second surface 213. The expansion layer 212 is coupled to a substrate cap 216 at the first surface 211 and to the adhesive layer 214 at the second surface 213 such that the expansion layer 212 is located between the cap 216 and the adhesive layer 214. The adhesive layer 214 includes a first surface 215 and a second surface 217. The thickness of the transfer film 200 is greater than approximately 10 µm, with the expansion layer 212 having a thickness of approximately 10–80 µm and the adhesive layer having a thickness of approximately 0.1–10 µm, preferably less than 5 µm.

The transfer film 200 is similar to the transfer film 100 described in FIGS. 2–4; however, the adhesive layer 214 includes additional retractive properties. The expansion layer 212 is a layer that expands when activated by the laser beam. The expansion layer 212 is capable of absorbing a sufficient amount of energy to expand and flow; and thereby, push upon a substantially unmelted adhesive layer 214 that is preferably not activated by a laser pulse 228. In one embodiment, a portion of the adhesive layer 214 that is pushed by the expansion layer 212 contacts the sample and adheres thereto as shown in FIG. 6. Hence, the adhesive layer 214 also provides adhesive qualities for microdissection. Upon adhesion to the sample 218, the adhesive layer 214 is partially retracted towards the substrate cap 216 by a retractive force 226 exerted by the unmelted adhesive layer 214 as shown in FIG. 7. Hence, the adhesive layer 214 also provides retraction qualities that enhance the mechanical response of the transfer film 200. After the target cells are adhered, it is desired that the transfer film 200 retract from the tissue sample 218 pulling the cells out of the sample. The thickness of the expansion layer 212 is approximately 20 $\mu$m to 30 $\mu$m. The thickness of the adhesive layer 214 is approximately 0.1–10 $\mu$m, preferably less than 5 $\mu$m. It is understood that the expansion layer 212 may be thermally coupled to at least one energy-absorbing substance of the type and in the manner discussed above. For example, thermal coupling can be accomplished by doping the layer 212 with one or more energy absorbing substances or by attaching an energy-absorbing layer of the type and the manner discussed above with respect to the expansion layer 112.

From a materials point of view, the choice of expansion layer 212 can be identical to its counterpart 112 of FIGS. 2–3 (as described above). The adhesive layer 214 is similar to the adhesive layer 114 of FIGS. 2–3 (i.e., it needs to effectively wet and adhere to the sample), however, additionally it must have retractive properties. As such, one needs an adhesive polymeric system that has unique viscoelastic properties. In particular, one needs an elastomeric material that contains partial cross-links, which in turn can be present either as chemical cross-links (e.g., silicone elastomers), or as physical cross-links (e.g., block copolymers). Chemical cross-linked systems include, but not limited to silicone elastomers, polyurethanes, polyureas, epoxies, various electron-beamed polymers (polyethylenes, polypropylenes, fluoropolymers), peroxide cross-linked vinyl-containing polymers. Physical cross-linked systems, include polymers such as, but not limited to rubbers (natural, butyl, or styrene-butadiene rubber), block copolymers such as styrene-ethylene/butadiene-styrene (SEBS), styrene-isoprene-styrene (SIS), polyisobutylene, and polybutenes can be employed. As before, various compatible tackifying agents in low to moderate ratios, as well as other commonly used additives, known to those skilled in the art of polymer formulation can be employed to achieve desired balance of materials properties. The adhesive layer 214 may be thermally coupled to at least one energy-absorbing substance as described above in reference to the adhesive layer 114. Preferably, the adhesive layer 214 is undoped such that it is not activated by the laser pulse and does not substantially plastically deform so that it may substantially elastically retract away from the sample 218. If the laser pulse is short enough to prevent heat deposited into the expansion layer 212 to propagate into the undoped adhesive layer 214, the adhesive layer 214 will not melt.

The basic mode of constructing and manufacturing the transfer film 200 is, as a first approximation, identical to that of the transfer film 100, as described above. The adhesive layer 214 can be doped in a homogenous fashion with at least one energy-absorptive substance of the type and in the manner described above. Alternatively, the transfer film 200 is formed by doping the adhesive layer 214 with at least one energy-absorptive substance of the type and in the manner described above to a desired depth to create a gradient in the adhesive layer 214 wherein the remaining un-doped portion forms the adhesive layer 214 similar to the embodiment shown in FIG. 4 where the adhesive layer 214 now includes retraction properties.

Figure 8:
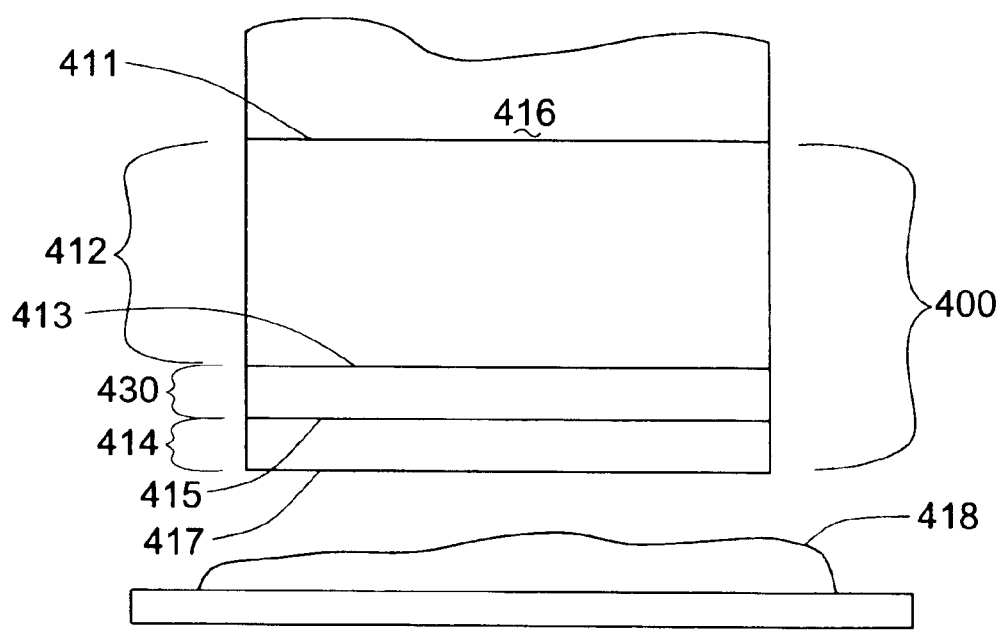
FIG. 8 is a side view of a transfer film, carrier, and sample of the present invention.
Figure 9:
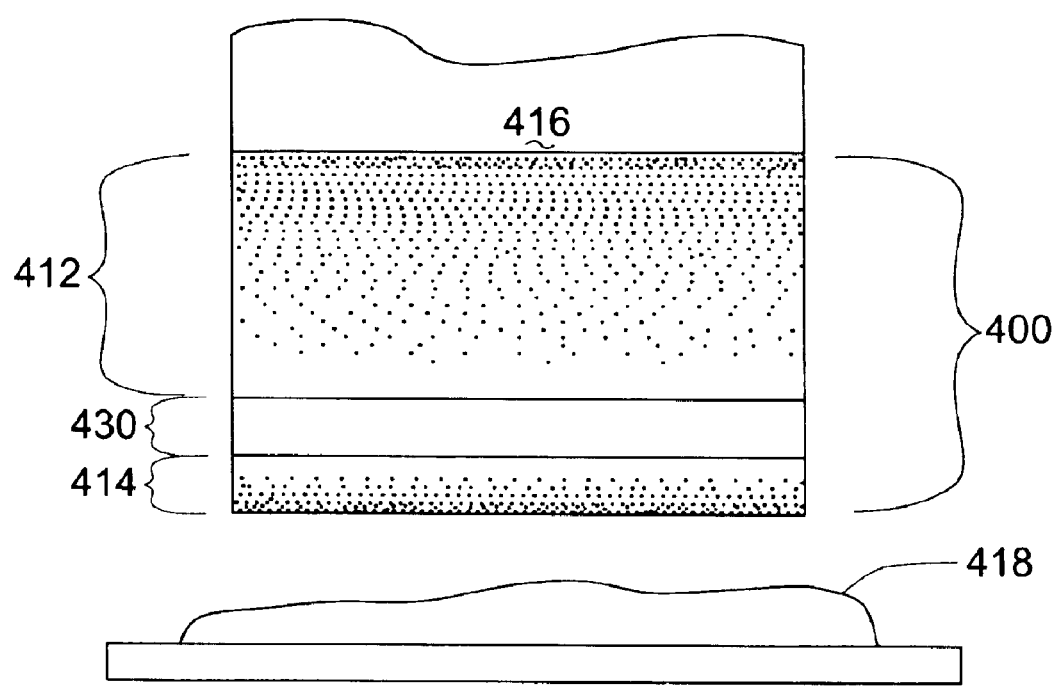
FIG. 9 is a side view of a transfer film, carrier, and sample of the present invention.

Referring now to FIGS. 8–9, there is shown a transfer film 400 wherein the retraction properties are de-coupled from the adhesive properties. The transfer film 400 includes an expansion layer 412, an adhesive layer 414 and a retraction layer 430. The expansion layer 412 includes a first surface 411 and a second surface 413. The expansion layer 412 is coupled to a substrate cap 416 at the first surface 411 and to the retraction layer 430 at the second surface 413 such that the expansion layer 412 is located between the cap 416 and the retraction layer 430. The adhesive layer 414 includes a first surface 415 and a second surface 417. The adhesive layer 414 is coupled to the retraction layer 430 such that the retraction layer 430 is located between the expansion layer 412 and the adhesive layer 414. The thickness of the transfer film 400 is greater than approximately 10 $\mu$m, with the expansion layer 412 having a thickness of approximately 10–80 $\mu$m, the retraction layer having a thickness of approximately 0.1–10 $\mu$m, preferably less than 5 $\mu$m, and the adhesive layer having a thickness of approximately 0.1–10 $\mu$m, preferably less than 5 $\mu$m.

The expansion layer 412 and the adhesive layer 414 is similar to the expansion layer 112 and adhesive layer 114, respectively, as discussed above. The expansion layer 412 is a layer that expands when activated by the laser beam. The expansion layer 412 is capable of absorbing a sufficient amount of energy to expand and flow; and thereby, push upon a preferably un-doped retraction layer 430 and, in turn, upon the adhesive layer 414. The retraction layer 430 is substantially unmelted and retains substantial elastic properties. The adhesive layer 414 is preferably not activated by the laser pulse. However, the invention is not so limited. In one embodiment, a portion of the adhesive layer 414 that is pushed by the expanding expansion layer 412 and retraction layer 430 contacts the sample 418 and adheres thereto. Upon adhesion to the sample 418, the adhesive layer 414 is partially retracted towards the substrate cap 216 by a retractive force 226 exerted by the substantially elastic retraction layer 414. Hence, the adhesive qualities and retractive qualities are separately provided by the adhesive layer 214 and the retractive layer 430, respectively. The mechanical response of the transfer film 200 is, thereby, enhanced. After the target cells are adhered, it is desired that the transfer film 400 retract from the tissue sample 418 pulling the cells out of the sample.

It is understood that the expansion layer 412 may be thermally coupled to at least one energy-absorbing substance of the type and in the manner discussed above. For example, thermal coupling can be accomplished by doping the layer 412 with one or more energy absorbing substances or by attaching an energy-absorbing layer of the type and the manner discussed above with respect to the expansion layer 112.

The adhesive layer 414 is similar to the adhesive layer 114 of FIGS. 2–4 and it may be thermally coupled to at least one energy-absorbing substance as described above and as shown in FIG. 2–4. Preferably, the adhesive layer 414 is un-doped such that it is not activated by the laser pulse and does not substantially plastically deform so that it may substantially elastically retract away from the sample 418. If the laser pulse is short enough to prevent heat deposited into the expansion layer 412 to propagate into the un-doped retractive layer 430 and adhesive layer 414. The adhesive layer 414 and the retraction layer 430 will not melt.

From a materials standpoint, property requirements and thus the choices are identical to other expansion layers described above. The retraction layer 430, once again, needs to have elastomeric properties, and thus, physically- and chemically-cross-linked systems similar to those described above can be utilized. Here, since the retraction layer 430 does not come into actual contact with the sample, it does not require to have adhesive properties, except in so far as its need to be adhered to its adjacent layers. As such, tackifying agents need not to be used in the formulation of this layer, although their use is not precluded in the present invention. Finally, the adhesive layer 414 can be made from any of the adhesive materials as in its counterpart, adhesive layer 114, as described in FIG. 2. In general, the softening point of the adhesive layer is preferably less than the softening point of the expansion layer.

The method of manufacturing the three-layer construction of this embodiment of the current patent utilizes identical polymer processing techniques to those described earlier for the two-layer counterparts. In particular, in one embodiment, the transfer film 400 is formed by doping the adhesive layer 414 with at least one energy-absorptive substance of the type and in the manner described above to a desired depth to create the expansion layer wherein the remaining un-doped portion forms the retraction and adhesive layers 430, 414.

Alternatively, in another embodiment of the invention, as shown in FIG. 9, the adhesive layer 414 is shown to be coupled to the retraction layer 430 of the transfer film 400 as a doped adhesive layer 414. Here, at least one concentration gradient may be formed by the doping method; however, the invention is not so limited and the energy-absorptive substance may be uniformly distributed throughout the expansion layer 412 and/or the adhesive layer 414 or include a discrete film of thermoplastic containing absorptive material thermally coupled to the adhesive layer 414 or a discrete metallic film layer thermally coupled to the adhesive layer 414.

Although FIGS. 2–9 depict the transfer film spaced from the sample, the invention is not so limited and contact laser micro-capture is within the scope of the present invention.

EXAMPLE 1

A prototype transfer film with one layer of dyed EVA (Elvax 40) as the expansion layer and one layer of nondyed polyisobutylene (Butyl 065) as the adhesive layer was prepared using manual hot pressing. Each film was compression molded separately, combined together, and applied to the cap with the expansion layer facing the cap.

The EVA film was compression molded at 130° C. and 4,000 psi for 3 minutes between 1 mil shims and cooled to room temperature. The polyisobutylene film was molded at 150° C. and 10,000 psi for 3 minutes between 1 mil shims and cooled to room temperature. The two film were then combined at 70° C. and 4,000 psi for 3 minutes between 2 mil shims and cooled to room temperature. A small diameter piece was punched out of the sheet and applied to the cap at 70° C. with light contact pressure for 3 minutes. The completed cap with laminate film was test fired 12 µm above a glass slide and a wetted spot was formed that adhered to the glass surface. Various diameters of wetted spots were formed depending on the energy of the targeting laser.

EXAMPLE 2

A prototype transfer film with one layer of dyed EVA (Elvax 410) as the expansion layer and one layer of nondyed polyisobutylene (Butyl 065) as the adhesive layer was prepared using a combination of automated hot pressing and spin coating. The EVA film was applied to the cap using standard manufacturing procedures. A 10% solution of polyisobutylene was dissolved in cyclohexane and applied to the EVA surface of the cap using a commercial spin coater, Headway Research, Inc. The cap was held to the spinning chuck by vacuum and ~50 µl of polyisobutylene solution was dispensed while the cap was spinning at 10,000 rpm. After spin coating, the cap was test fired fired 12 µm above a glass slide and a wetted spot was formed that adhered to the glass surface. Various diameters of wetted spots were formed depending on the energy of the targeting laser.

EXAMPLE 3

A prototype transfer film with one layer of dyed EVA (Elvax 410) as the expansion layer and one layer of block copolymer based pressure sensitive adhesive (PSA) as the adhesive layer was prepared using a combination of automated hot pressing solvent spin coating techniques. The EVA film was applied to the cap using standard manufacturing procedures. For the adhesive layer, a polymer solution was first made from 10 wt/vol % of a Kraton 1107/Escorez 1310 in Toluene. Kraton 1107 is a block copolymer-based (styrene-isoprene-styrene) thermoplastic rubber supplied by Kroton Polymer. Escorez 1107 is an aliphatic tackifier resin supplied by ExxonMobil Chemicals. The ratio of Kraton 110 to Escorez 1310 was 1/1, based on weights. The resulting polymeric solution was then applied dynamically (as opposed to statically at the beginning of the experiment) to the EVA surface of the cap using a commercial spin coater, Headway Research, Inc. The cap was held to the spinning chuck by vacuum and 100 µl of the polymer solution was dispensed while the cap was spinning at 10,000 rpm and continued to spin for 10 minutes. The acceleration and deceleration rates were both 1000 rmp/sec. The resulting two-layer film has a thin (micron-level) layer of PSA, and as such has a considerably higher tack associated with it, as compared to the original (underlying) EVA film, which is now utilized as the expansion layer. After spin coating, the cap was test fired 12 µm above a glass slide and a wetted spot was formed that adhered to the glass surface. Various diameters of wetted spots were formed depending on the energy of the targeting laser. Separately various frozen-sectioned tissues such as prostate, colon, and skin were successfully microdissected using this 2-layer transfer film.

While the present invention has been described with reference to one or more particular variations, those skilled in the art will recognize that many changes may be made thereto without departing from the spirit and scope of the present invention. Furthermore, while the invention is described with respect to biological samples, it is understood that the invention is not so limited and that any sample, including non-biological samples that lend themselves to laser micro-capture, with or without dissection, can be employed and are within the scope of the invention.

Each of these embodiments and obvious variations thereof are contemplated as falling within the spirit and scope of the claimed invention, which is set forth in the following claims.

What is claimed is:

1. A method for laser micro-capture comprising: providing a sample,
   placing the sample in the optical path of an optical system,
   placing a transfer film within the optical path of the system; the transfer film comprising at least one energy absorbing substance and, at least one expansion layer and at least one adhesive layer; the adhesive layer being located between the expansion layer and the sample selecting a portion of the sample for micro-capture; exposing the at least one energy absorbing substance to energy capable of activating the transfer film resulting in expansion of the expansion layer to exert a force upon the adhesive layer such that a selected portion of the sample adheres to the adhesive layer for micro-capture.

2. The method of claim 1, wherein the transfer film retracts subsequent to adhesion of the adhesive layer to the sample.

3. The method of claim 1, wherein the step of exposing the at least one energy absorbing substance to energy includes exposing with more than one pulse of energy for independently addressing more than one energy absorbing substance.

4. A transfer film for laser micro-capture of a sample comprising:
at least one expansion layer, and
an outer adhesive layer coupled to one side of the expansion layer; the adhesive layer being located between the expansion layer and the sample for micro-capture;
the expansion layer being adapted to absorb energy incident upon the transfer film and to expand to exert a force upon the adhesive layer such that the adhesive layer is deflected towards a selected portion of the sample; the adhesive layer being adapted to adhere to the selected portion of the sample for micro-capture.

5. The transfer film of claim 4, wherein the adhesive layer includes at least one pressure sensitive adhesive.

6. The transfer film of claim 4, wherein at least one of the layers includes a polymer selected from the group consisting of thermosets, thermoplastics, and elastomers.

7. The transfer film of claim 4, wherein the expansion layer is thermally coupled to at least one energy absorbing substance.

8. The transfer film of claim 4, wherein at least one energy absorbing substance is thermally coupled to the expansion layer, and at least one energy absorbing substance is thermally coupled to the adhesive layer and the at least one energy absorbing substance coupled to the expansion layer is addressable independently from the at least one energy absorbing substance coupled to the adhesive layer.

9. The transfer film of claim 7, wherein the expansion layer is doped with at least one energy absorbing substance and the adhesive layer is not doped.

10. The transfer film of claim 8, wherein the at least one energy absorbing substance that is coupled to the expansion layer is addressable independently from the at least one energy absorbing substance coupled to the adhesive layer such that activation of the expansion layer provides a first expansion towards the sample having at least a first distance and activation of the adhesive layer provides a second expansion towards the sample having at least a second distance.

11. The transfer film according to claims 7 or 8, wherein the at least one energy absorbing substance is selected from the group consisting of energy absorbing dyes, metal films, polymer nano-composites, and Buckminsterfullerene.

12. The transfer film according to claims 7 or 8, wherein the energy absorbing substance forms at least one concentration gradient.

13. The transfer film of claim 4, wherein the transfer film is adapted to retract away from the sample.

14. The transfer film of claim 13, wherein the transfer film comprises a retraction layer located between the expansion layer and the adhesive layer.

15. The transfer film of claim 14, wherein at least one of the layers includes a polymer selected from the group consisting of thermosets, thermoplastics, and elastomers.

16. The transfer film of claim 14, wherein the retraction layer is coupled to at least one energy absorbing substance.

17. The transfer film of claim 16, wherein the energy absorbing substance coupled to the retraction layer is independently addressable.

* * * * *

UNITED STATES PATENT AND TRADEMARK OFFICE
CERTIFICATE OF CORRECTION

PATENT NO.   : 6,887,703 B2               Page 1 of 1
DATED        : May 3, 2005
INVENTOR(S)  : Thomas M. Baer et al.

It is certified that error appears in the above-identified patent and that said Letters Patent is hereby corrected as shown below:

Title page,
Item [75], Inventor, "Barbara J. Wessen-Baer" should read -- Barbara J. Weesen-Baer --.
Item [73], Assignee, "Arturus Bioscience, Inc." should read -- Arcturus Bioscience, Inc. --.

Signed and Sealed this

Twenty-fifth Day of April, 2006

JON W. DUDAS
*Director of the United States Patent and Trademark Office*